(12) United States Patent
Kim

(10) Patent No.: US 12,249,007 B2
(45) Date of Patent: Mar. 11, 2025

(54) MAGNETIC RESONANCE IMAGE PROCESSING METHOD AND APPARATUS USING SCAN PARAMETERS

(71) Applicant: AIRS MEDICAL INC., Seoul (KR)

(72) Inventor: Jeewook Kim, Seoul (KR)

(73) Assignee: AIRS MEDICAL INC., Seoul (KR)

(*) Notice: Subject to any disclaimer, the term of this patent is extended or adjusted under 35 U.S.C. 154(b) by 0 days.

(21) Appl. No.: 17/790,832

(22) PCT Filed: Apr. 21, 2022

(86) PCT No.: PCT/KR2022/005705
§ 371 (c)(1),
(2) Date: Jul. 5, 2022

(87) PCT Pub. No.: WO2023/128074
PCT Pub. Date: Jul. 6, 2023

(65) Prior Publication Data
US 2024/0127498 A1    Apr. 18, 2024

(30) Foreign Application Priority Data
Dec. 30, 2021 (KR) .................. 10-2021-0192564

(51) Int. Cl.
A61B 5/055     (2006.01)
G06T 11/00    (2006.01)

(52) U.S. Cl.
CPC .......... G06T 11/006 (2013.01); G06T 11/005 (2013.01); G06T 2210/41 (2013.01); G06T 2211/441 (2023.08)

(58) Field of Classification Search
None
See application file for complete search history.

(56) References Cited

U.S. PATENT DOCUMENTS

| | | | |
|---|---|---|---|
| 2019/0219654 A1* | 7/2019 | Park | G01R 33/56554 |
| 2020/0217914 A1* | 7/2020 | Huang | G01R 33/561 |
| 2020/0400767 A1* | 12/2020 | Venkatesan | G06N 3/08 |
| 2021/0065413 A1* | 3/2021 | Huang | G16H 30/40 |
| 2022/0075017 A1* | 3/2022 | Sabuncu | G01R 33/561 |
| 2022/0156896 A1* | 5/2022 | Li | G06T 5/50 |

(Continued)

FOREIGN PATENT DOCUMENTS

| | | | | |
|---|---|---|---|---|
| CN | 113298710 A | * | 8/2021 | .......... G06T 3/4053 |
| JP | 6560023 B2 | | 8/2019 | |
| JP | 6772112 B2 | | 10/2020 | |

(Continued)

*Primary Examiner* — Amandeep Saini
*Assistant Examiner* — Caroline Tabancay Duffy
(74) *Attorney, Agent, or Firm* — Harness, Dickey & Pierce, P.L.C.

(57) ABSTRACT

According to an embodiment of the present invention, there is provided a magnetic resonance image processing method including: acquiring a low-quality training image, a first parameter group including at least one scan parameter applied when the training image is acquired, a high-quality label image, and a second parameter group including at least one scan parameter applied when the label image is acquired; and training an artificial neural network model by using the training image, the first parameter group, the label image, and the second parameter group.

12 Claims, 10 Drawing Sheets

(56) References Cited

U.S. PATENT DOCUMENTS

2023/0168327 A1* 6/2023 Wyss ....................... G06N 3/02
                                                    324/309
2023/0181074 A1* 6/2023 Amthor ................ A61B 5/7275
                                                    600/411

FOREIGN PATENT DOCUMENTS

| KR | 10-1923184 | B1 | 11/2018 |
| KR | 10-2144320 | B1 | 8/2020 |
| KR | 10-2258756 | B1 | 5/2021 |

* cited by examiner

IMAGE DOMAIN

MAGNETIC RESONANCE IMAGE PROCESSING METHOD AND APPARATUS USING SCAN PARAMETERS

CROSS-REFERENCE TO RELATED APPLICATION

This application is a national phase entry of PCT Application No. PCT/KR2022/005705, filed on 21 Apr. 2022 and claims priority to Korean Patent Application No. 10-2021-0192564, filed on 30 Dec. 2021. The entire disclosures of the applications identified in this paragraph are incorporated herein by references.

TECHNICAL FIELD

The present invention relates to a magnetic resonance image processing method and apparatus, and more particularly to a magnetic resonance image processing method and apparatus that acquire a magnetic resonance image by training an artificial neural network using scan parameters.

BACKGROUND ART

In general, medical imaging machines are apparatuses that acquire information about the body of a patient and provide an image. Medical imaging machines include X-ray machines, ultrasound diagnostic scanners, computed tomography scanners, magnetic resonance imaging (MRI) machines, etc.

In this case, a magnetic resonance image is an image acquired by imaging the density and physical/chemical properties of atomic nuclei by generating nuclear magnetic resonance in the atomic nuclei nucleus of hydrogen in the human body using a magnetic field and non-ionizing radiation that are harmless to the human body. Magnetic resonance imaging machines occupy an important position in the field of diagnosis using medical images because the imaging conditions thereof are relatively free and they provide images including various types of diagnostic information from soft tissues and having desirable contrast.

Meanwhile, in order to acquire desired data, a photographer may perform magnetic resonance imaging after specifically setting parameters representative of imaging conditions. When the parameters are changed, an acquired magnetic resonance signal is changed, and thus tasks to be performed for image reconstruction may be changed. In other words, it is necessary to perform image reconstruction by taking into consideration not only the magnetic resonance signal but also the parameters used to perform imaging.

SUMMARY

Technical Problem

The present invention intends to solve the above-described problems of the related art, and is directed to a magnetic resonance image processing method and apparatus using scan parameters that reconstruct a magnetic resonance image by using scan parameters used to acquire the magnetic resonance image.

However, the technical problems to be solved by the present embodiment are not limited to the above-described technical problem, and another technical problem may be present.

Technical Solution

As a technical solution for solving the above-described technical problem, according to an embodiment of the present invention, there is provided a magnetic resonance image processing method including: acquiring a low-quality training image, a first parameter group including at least one scan parameter applied when the training image is acquired, a high-quality label image, and a second parameter group including at least one scan parameter applied when the label image is acquired; and training an artificial neural network model by using the training image, the first parameter group, the label image, and the second parameter group.

As an embodiment, the scan parameter may include at least one of: the number of excitations, which is the number of repetitions at the time when lines of first k-space data of a magnetic resonance signal are repeatedly acquired; a phase resolution, which is a value obtained by dividing the number of lines sampled in a phase encoding direction of the first k-space data by a preset reference value; and an acceleration factor, which refers to a value obtained by dividing the number of fully sampled signal lines of the first k-space data by the number of sub-sampled signal lines.

As an embodiment, the training image may be acquired by sub-sampling a magnetic resonance signal, and the label image may be acquired by fully sampling the magnetic resonance signal.

As an embodiment, the number of excitations of the training image may be smaller than the number of excitations of the label image.

As an embodiment, the phase resolution of the training image may be lower than the phase resolution of the label image. As an embodiment, training the artificial neural network model may include performing pre-processing so that the size of the first parameter group and the size of the second parameter group correspond to the number of channels of the artificial neural network model.

As an embodiment, performing the pre-processing may include generating first attention data and second attention data by inputting the first parameter group and the second parameter group to a pre-processing artificial neural network model, and training the artificial neural network model may include inputting the first attention data and the second attention data to the artificial neural network model.

As an embodiment, the pre-processing artificial neural network model may include a fully connected layer.

As an embodiment, the magnetic resonance image processing method may further include generating a reconstructed image by inputting an input image and a third parameter group, including at least one scan parameter applied when the input image is acquired, to the artificial neural network model.

As a technical solution for solving the above-described technical problem, according to an embodiment of the present invention, there is provided a magnetic resonance image processing method including: inputting an input image and a third parameter group, including at least one scan parameter applied when the input image is acquired, to an artificial neural network model trained using a low-quality training image, a first parameter group including at least one scan parameter applied when the training image is acquired, a high-quality label image, and a second parameter group including at least one scan parameter applied when the label image is acquired; and outputting a reconstructed image from the artificial neural network model.

As a technical solution for solving the above-described technical problem, according to an embodiment of the present invention, there is provided a magnetic resonance image processing apparatus for performing a magnetic resonance image processing method, the magnetic resonance image processing apparatus including: memory configured to store a magnetic resonance image processing program; and a processor configured to execute the program; wherein the processor trains an artificial neural network model by using a low-quality training image, a first parameter group including at least one scan parameter applied when the training image is acquired, a high-quality label image, and a second parameter group including at least one scan parameter applied when the label image is acquired.

Advantageous Effects

According to the above-described technical solutions of the present invention, the present invention trains an artificial neural network by using not only a magnetic resonance signal but also scan parameters used to perform imaging, thereby improving the accuracy of a magnetic resonance image acquired using the artificial neural network.

In addition, a magnetic resonance image can be reconstructed such that data desired by a user is emphasized by adjusting the values of scan parameters used for training, thereby increasing the convenience of the user.

DETAILED DESCRIPTION

Figure 1:
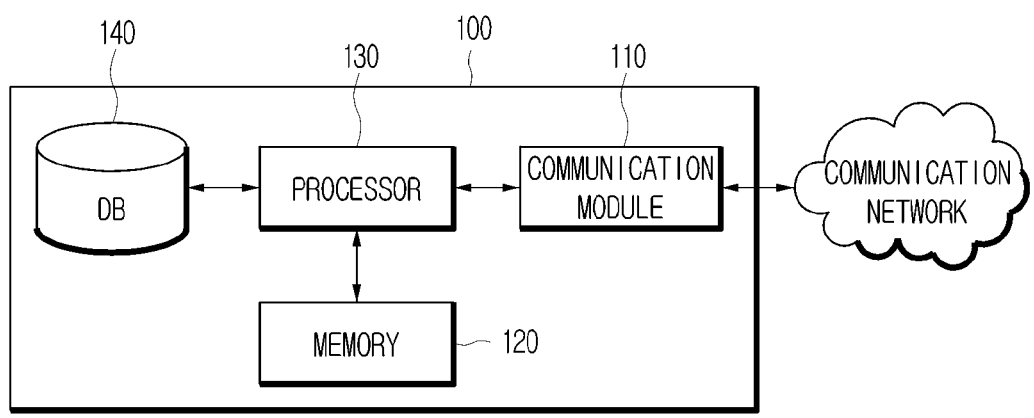
FIG. 1 is a diagram showing the configuration of a magnetic resonance image processing apparatus according to an embodiment of the present invention.

Embodiments of the present invention will be described in detail below with reference to the accompanying drawings so that those of ordinary skill in the art to which the present invention pertains may easily practice the present invention. However, the present invention may be implemented in various different forms, and is not limited to the embodiments described herein. Furthermore, in the drawings, portions not related to the description are omitted for the clear description of the present invention, and like reference numerals are assigned to like portions throughout the specification.

The specification does not describe all the components of the embodiments, and descriptions common in the art to which the present invention pertains or overlap descriptions between embodiments are omitted. The term 'unit' used herein may be implemented as software or hardware. According to embodiments, a plurality of 'units' may be implemented as a single component or one 'unit' may include a plurality of components.

In the present specification, the 'image' may refer to multi-dimensional data composed of discrete image elements (e.g., pixels in a 2D image or voxels in a 3D image). For example, an image may include medical images acquired by medical imaging machines such as a magnetic resonance imaging (MRI) machine, a computed tomography (CT) scanner, an ultrasonic scanner, and an X-ray machine.

In the present specification, the 'object' is a target for imaging, and may include a human, an animal, or a part thereof. For example, an object may include a part (organ) of the body or a phantom. The phantom refers to a volume material having a density and an effective atomic number considerably close to those of an organism, and may include a spherical phantom having properties similar to those of the body.

A magnetic resonance image (MRI) system is a system that acquires images of tomographic areas of an object by representing the intensity of a magnetic resonance (MR) signal for a radio frequency (RF) signal generated from a magnetic field having a specific intensity in the form of contrasts between light and darkness.

The MRI system allows a main magnet to form a static magnetic field, and aligns the magnetic dipole moment direction of a specific atomic nucleus of an object, located in the static magnetic field, in the direction of the static magnetic field. A gradient magnetic field coil may generate a gradient magnetic field by applying a gradient signal to the static magnetic field, thereby inducing a different resonance frequency for each portion of the object. An RF coil may radiate a magnetic resonance signal in accordance with the resonance frequency of a portion where an image is to be acquired. Furthermore, as the gradient magnetic field is formed, the RF coil may receive magnetic resonance signals of different resonance frequencies radiated from various portions of the object. The MRI system acquires an image by applying an image reconstruction technique to the magnetic resonance signals received through this step. In addition, the MRI system may reconstruct a plurality of magnetic resonance signals into image data by performing serial or parallel signal processing on the plurality of magnetic resonance signals received by multi-channel RF coils.

A magnetic resonance image processing apparatus according to an embodiment of the present invention will be described below.

FIG. 1 is a diagram showing the configuration of a magnetic resonance image processing apparatus according to an embodiment of the present invention.

Referring to FIG. 1, a magnetic resonance image processing apparatus 100 may include not only an MRI system capable of acquiring a magnetic resonance image by detecting a magnetic resonance signal by itself, but also an image processing apparatus for processing an image acquired from the outside, and a smartphone, a tablet personal computer (PC), a PC, a smart TV, a micro-server, a cloud server, other home appliances, and other mobile or non-mobile computing devices equipped with a function of processing a magnetic resonance image, but is not limited thereto. In addition, the magnetic resonance image processing apparatus 100 may be a wearable device, such as a watch, glasses, a hairband, or a ring, equipped with a communication function and a data processing function.

Furthermore, the magnetic resonance image processing apparatus 100 according to an embodiment of the present invention may be directed to a magnetic resonance image processing apparatus 100 that transmits and receives medical image data while communicating with a picture archiving and communication system (PACS) or a magnetic resonance imaging apparatus 100 used in a medical institution and reconstructs magnetic resonance image data by using an artificial neural network model.

In addition, the magnetic resonance image processing apparatus 100 according to an embodiment of the present invention may be implemented in the form of a cloud computing system. Cloud computing is a computing environment in which IT-related services such as data storage, networking, and the use of content can be used in an integrated manner through a server on the Internet. Alternatively, the magnetic resonance image processing apparatus 100 may be implemented as various types of computing systems capable of performing a magnetic resonance image processing method such as server computing, edge computing, and serverless computing.

More specifically, the magnetic resonance image processing apparatus 100 according to an embodiment of the present invention may include a communication module 110, memory 120, a processor 130, and a database 140.

The communication module 110 provides a communication interface to the magnetic resonance image processing apparatus while operating in conjunction with a communication network. The magnetic resonance image processing apparatus 100 may transmit and receive data to and from a client terminal, a PACS terminal, and a PACS server to be described later by using the communication module 110. In this case, the communication module 110 may be a device including hardware and software necessary to transmit and receive signals, such as control signals or data signals, to and from another network device over a wired/wireless connection.

For example, the communication module 110 may perform communication via a local area network (LAN), Wideband Code Division Multiple Access (WCDMA), Long Term Evolution (LTE), wireless broadband (WiBro), the 5-th generation mobile communication (5G), ultra-wideband (UWB), ZigBee, radio frequency (RF) communication, a wireless LAN, Wireless Fidelity (Wi-Fi), near-field communication (NFC), Bluetooth, infrared communication, etc. However, this is an example, and various wired/wireless communication technologies applicable in the art may be used according to an embodiment to which the present invention is applied.

Meanwhile, in the present invention, the 'terminal' may be a wireless communication device with guaranteed portability and mobility, and may be one of all types of handheld-based wireless communication devices such as a smartphone, a tablet PC, or a notebook. Furthermore, the 'terminal' may be a wearable device, such as a watch, glasses, a hairband or a ring, equipped with a communication function and a data processing function. Moreover, the 'terminal' may be a wired communication device, such as a PC, that can be connected to another terminal or a server over a network.

A client terminal configured to control an medical imaging machine or manage the transmission of medical image data in conjunction with the medical imaging machine and a PACS terminal installed with a PACS program and configured to allow medical staff to view, process, and manage medical image data may be generally deployed in a medical institution. The client terminal may be a terminal on which a program providing a user interface (UI) configured to output user login, a worklist, and image processing details is installed. The PACS terminal may be a terminal on which a program providing a user interface configured to transmit medical image data and personal information data, stored in the PACS server, to the magnetic resonance image processing apparatus 100 and to receive the medical image data reconstructed via an artificial neural network model and then store it in the PACS server or output it to a display is installed.

The memory 120 may be a storage medium in which a magnetic resonance image processing program is recorded. Furthermore, the memory 120 may perform a function of temporarily or permanently storing data that is processed by the processor. In this case, although the memory 120 may include volatile storage media or nonvolatile storage media, the scope of the present invention is not limited thereto. As used herein, the term "storage medium" refers to a non-transitory computer-readable medium, such as a hard disk, flash memory, or other tangible storage device capable of storing data. This excludes transitory signals, such as carrier waves, that are not within the scope of the present invention.

The processor 130 may control an overall process that is performed by the magnetic resonance image processing program in the magnetic resonance image processing apparatus 100. The individual steps of the process that is performed by the processor 130 will be described later.

In this case, the processor 130 may include all types of devices capable of processing data, such as a processor. In this case, for example, the 'processor' may refer to a data processing device embedded in hardware, which has circuits physically structured to perform functions represented by codes or instructions included in a program. Although as an example of the data processing device embedded in hardware as described above, processing devices such as a microprocessor, a central processing unit (CPU), a processor core, a multiprocessor, an application-specific integrated circuit (ASIC), and a field-programmable gate array (FPGA), may be enumerated, the scope of the present invention is not limited thereto.

The database 140 may be a component in which various types of data necessary for the magnetic resonance image processing apparatus 100 to execute a program are stored. For example, the database 140 may be a component in which the training data of an artificial neural network, magnetic resonance signal data, k-space data, and magnetic resonance image data are stored.

A method of acquiring a magnetic resonance image by performing accelerated imaging will be described in detail below with reference to FIGS. 2 to 6.

Figure 2A:
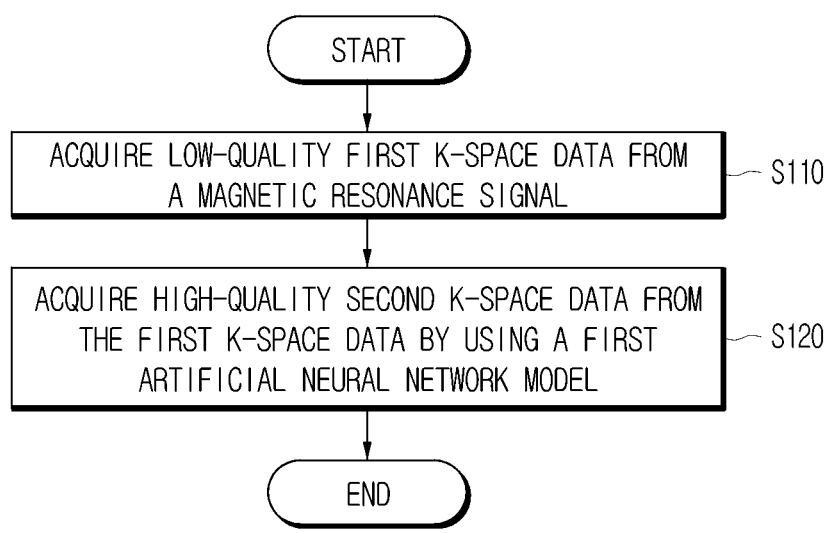
FIGS. 2a and 2b are diagrams showing a magnetic resonance image processing method in a k-space domain according to an embodiment of the present invention.
Figure 2B:
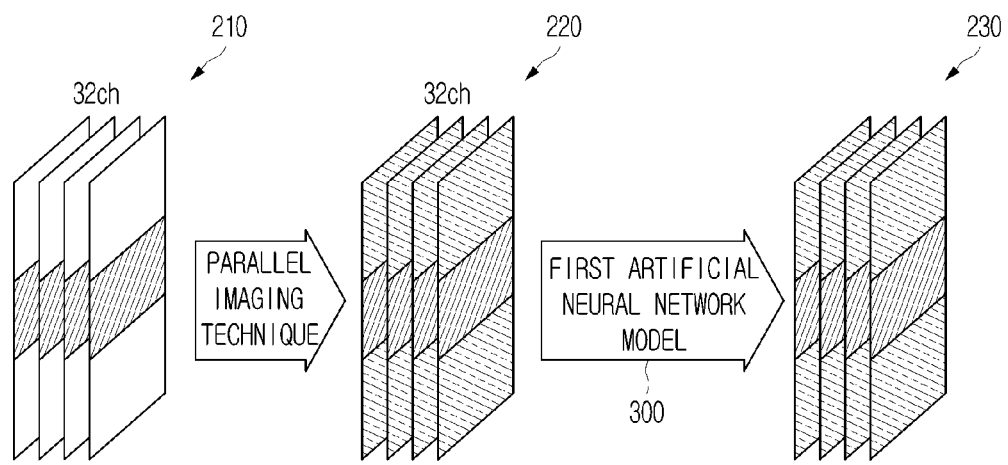
Figure 3A:
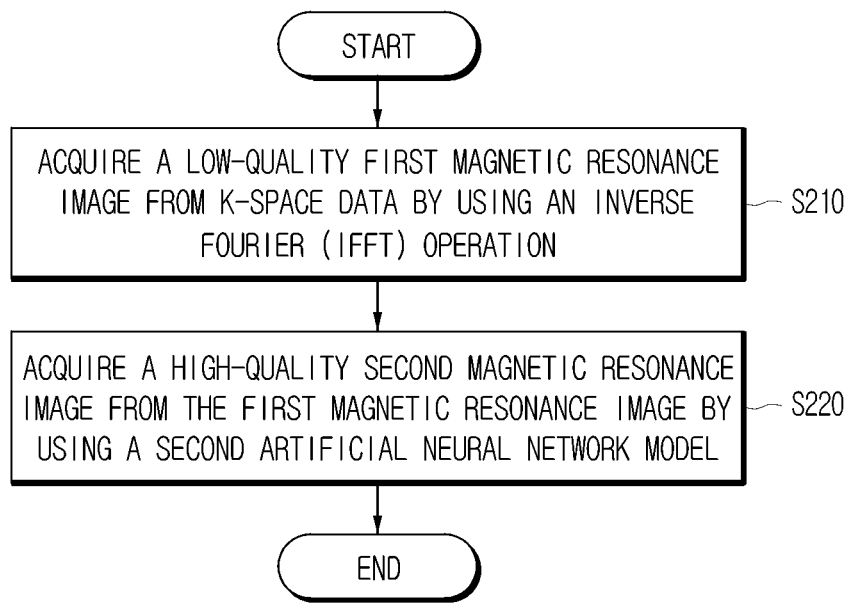
FIGS. 3a and 3b are diagrams showing a magnetic resonance image processing method in an image domain according to an embodiment of the present invention.
Figure 3B:
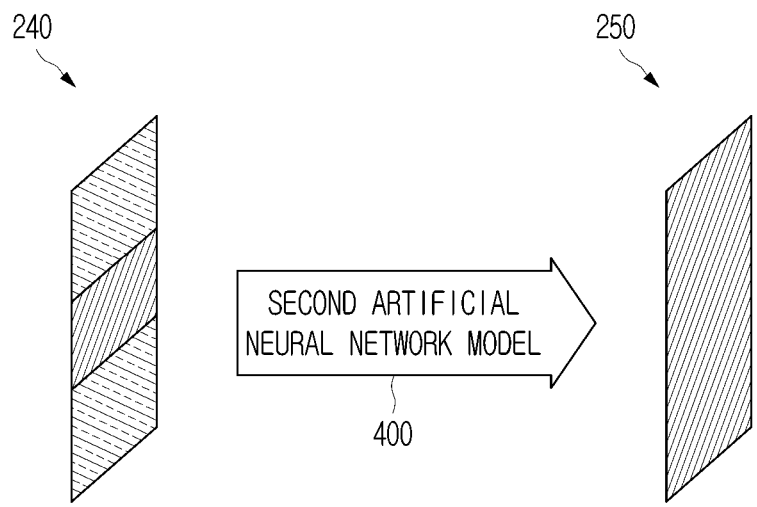
Figure 4:
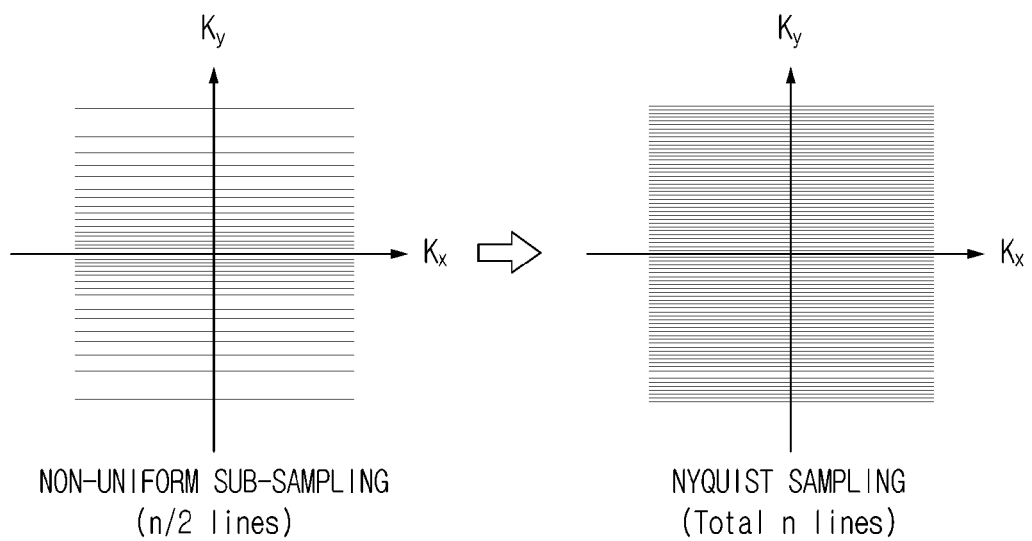
FIG. 4 is a schematic diagram illustrating the differences between sub-sampling and full sampling according to an embodiment of the present invention.
Figure 5:
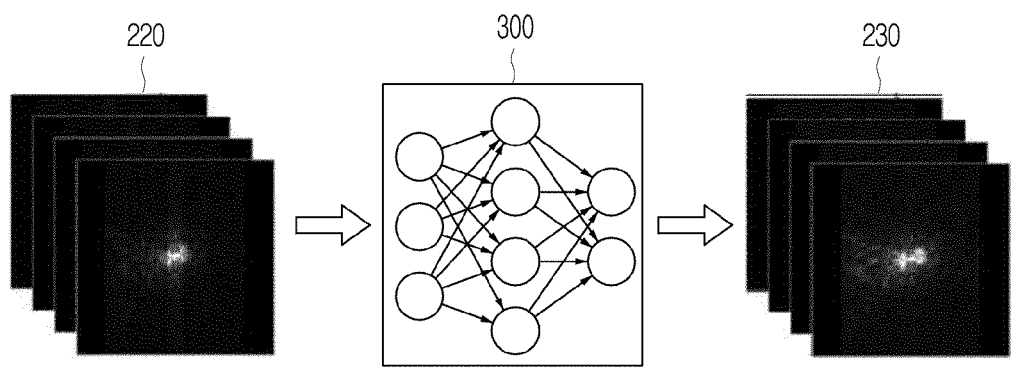
FIG. 5 is a schematic diagram showing the acquisition of second k-space data from first k-space data using a first artificial neural network model according to an embodiment of the present invention.
Figure 6:
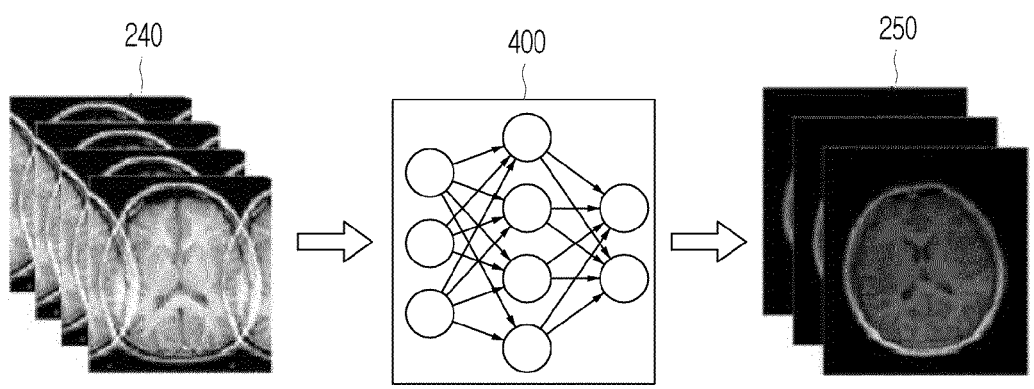
FIG. 6 is a schematic diagram showing the acquisition of a second magnetic resonance image from a first magnetic resonance image using a second artificial neural network model according to an embodiment of the present invention.

FIGS. 2a and 2b are diagrams showing a magnetic resonance image processing method in a k-space domain according to an embodiment of the present invention, FIGS. 3a and 3b are diagrams showing a magnetic resonance image processing method in an image domain according to an embodiment of the present invention, FIG. 4 is a schematic diagram illustrating the differences between subsampling and full sampling according to an embodiment of the present invention, FIG. 5 is a schematic diagram showing the acquisition of second k-space data from first k-space data using a first artificial neural network model according to an embodiment of the present invention, and FIG. 6 is a schematic diagram showing the acquisition of a second magnetic resonance image from a first magnetic resonance image using a second artificial neural network model according to an embodiment of the present invention.

In the present specification, imaging in which a magnetic resonance image is acquired using a sub-sampled magnetic resonance signal is referred to as accelerated imaging.

Accelerated imaging may refer to imaging in which an acquired magnetic resonance signal is reduced compared to general imaging. For example, general imaging may refer to acquiring a fully sampled magnetic resonance signal, whereas accelerated imaging may refer to acquiring a sub-sampled magnetic resonance signal. For example, general imaging may be imaging that takes 1 hour to acquire a 100% magnetic resonance signal, whereas accelerated imaging may be imaging that takes 30 minutes to acquire 50% magnetic resonance signal. Accordingly, a high-quality magnetic resonance image may be acquired through general imaging, whereas a relatively low-quality magnetic resonance image may be acquired through accelerated imaging. The low-quality magnetic resonance image may refer to an image having a lower resolution than a high-quality magnetic resonance image, or may refer to an image including more noise.

As an example, accelerated imaging may be imaging in which the number of excitations (NEX) is reduced compared to imaging used clinically. As an example, accelerated imaging may be imaging in which a phase resolution is reduced compared to imaging used clinically. As an example, accelerated imaging may be imaging in which an acceleration factor is increased and a parallel imaging technique is applied compared to imaging used clinically. Furthermore, an accelerated image may include not only an image taken by an actual magnetic resonance imaging machine but also an image acquired by processing an image, taken generally through computer simulation, to be identical or similar to an image taken through accelerated imaging.

Referring to FIGS. 2a and 2b, in the magnetic resonance image processing method performed by the magnetic resonance image processing apparatus according to an embodiment of the present invention, the step of acquiring the sub-sampled magnetic resonance signal 210 through accelerated imaging may be performed before step S110.

Referring to FIG. 4, the sub-sampled magnetic resonance signal 210 may be a magnetic resonance signal sampled at a sampling rate lower than the Nyquist sampling rate. Furthermore, the sub-sampled magnetic resonance image is an image acquired by sampling a magnetic resonance signal at a sampling rate lower than the Nyquist sampling rate. Meanwhile, a fully sampled magnetic resonance image may be an image acquired by sampling k-space data at a sampling rate equal to or higher than the Nyquist sampling rate.

For example, the number of lines of a fully sampled magnetic resonance signal may be n, and the number of lines of a sub-sampled magnetic resonance signal may be n/2. In this case, when the degree of reduction in the number of sampling lines is a multiple of ½, the acceleration factor of magnetic resonance imaging may be considered to be 2. When the degree of reduction in the number of sampling lines is a multiple of ⅓ or a multiple of ¼, the acceleration factor may be considered to be 3 or 4.

Furthermore, sub-sampling methods may be divided into uniform sub-sampling and non-uniform sub-sampling. The uniform sub-sampling may be a method of performing sampling while maintaining the constant interval of lines to be sampled. In contrast, the non-uniform sub-sampling may refer to a method of performing more sampling while decreasing the interval of lines to be sampled in a direction toward the center of sampling target data and performing less sampling while increasing the interval of lines to be sampled in a direction away from the center.

Meanwhile, the magnetic resonance image processing apparatus may be included in an MRI system, and may acquire input data corresponding to the sub-sampled magnetic resonance signal 210 based on the magnetic resonance signal received from an RF coil. In addition, the magnetic resonance image processing apparatus may acquire input data corresponding to the sub-sampled magnetic resonance signal 210 from at least one of an external magnetic resonance imaging machine, an external server, and a database.

Referring back to FIGS. 2a and 2b, there may be performed step S110 of acquiring first k-space data 220 from the sub-sampled magnetic resonance signal 210 by using a parallel imaging technique.

In this case, the parallel imaging technique is a type of image reconstruction technique for acquiring high-accuracy k-space data and/or a high-accuracy magnetic resonance image, such as fully sampled k-space data and/or a magnetic resonance image, from the sub-sampled magnetic resonance signal 210 and/or k-space data.

In the performance of image reconstruction according to the parallel imaging technique, known technologies, i.e., Sensitivity Profiles From an Array of Coils for Encoding and Reconstruction in Parallel (SPACE RIP), Simultaneous acquisition of spatial harmonics (SMASH), Partially Parallel Imaging With Localized Sensitivities (PILS), Generalized Autocalibrating Partially Parallel Acquisitions (GRAPPA), and Iterative Self-consistent Parallel Imaging Reconstruction (SPIRiT), may be applied without limitations as long as they can be applied to the parallel imaging technique.

After step S110, there may be performed step S120 of acquiring second k-space data 230 from the first k-space data 220 by using a first artificial neural network model 300.

Referring to FIG. 5, the first artificial neural network model 300 may be a set of algorithms for learning the correlation between at least one piece of sub-sampled first k-space data and at least one piece of fully sampled first k-space data by using statistical machine learning results. The first artificial neural network model 300 may include at least one neural network. The neural network may include network models such as a Deep Neural Network (DNN), a Recurrent Neural Network (RNN), a Bidirectional Recurrent Deep Neural Network (BRDNN), a Multilayer Perceptron (MLP) network, a Convolutional Neural Network (CNN), and U-net, but is not limited thereto.

For example, the first artificial neural network model 300 may be a model constructed by learning the correlation between at least one piece of sub-sampled first k-space data and at least one piece of fully sampled first k-space data using a neural network on the basis of every pixels of at least one sampling line stacked along a phase encoding direction Ky.

Referring to FIG. 4, the phase encoding direction Ky may be a direction extending parallel to a direction in which sampled lines are stacked in the process of sampling a magnetic resonance signal. In addition, a readout direction Kx may be a direction in which the sampled lines extend. Meanwhile, a Kz direction may be referred to as the axial direction of the coil or as a first direction Kz that is orthogonal to the phase encoding direction Ky and the readout direction Kx, which will be described later.

Meanwhile, when there is a plurality of sub-sampled magnetic resonance signals, pluralities of pieces of first k-space data 220 and second k-space data 230 may be acquired. In other words, when there is a plurality of RF coils for receiving magnetic resonance signals, a plurality of reconstructed images generated in response to a plurality of magnetic resonance signals received for respective channels become first magnetic resonance images.

Furthermore, the first artificial neural network model 300 may be constructed using various types of additional data other than the sub-sampled first k-space data and the fully sampled first k-space data. For example, at least one of real data, imaginary data, magnitude data, and phase data corresponding to the first k-space data 220 may be used as the additional data.

According to an embodiment of the present invention, the first artificial neural network model 300 may be trained according to a method to be described later with reference to FIGS. 7 to 9, and may generate the high-quality second k-space data 230 from the low-quality first k-space data 220.

Referring to FIGS. 3a and 3b, there may be performed step S210 of acquiring a first magnetic resonance image 240 from arbitrary k-space data by using an inverse Fourier (IFFT) operation. GRAPPA and/or an artificial neural network model may generate the first magnetic resonance image 240, i.e., a reconstructed image, by performing an inverse Fourier transform on image data in a complete k-space form.

After step S210, there may be performed step S220 of acquiring a second magnetic resonance image 250 from the first magnetic resonance image 240 by using a second artificial neural network model 400.

Referring to FIG. 6, the second artificial neural network model 400 may be a set of algorithms for learning the correlation between at least one sub-sampled magnetic resonance image and at least one fully sampled magnetic resonance image by using statistical machine learning results.

The second artificial neural network model 400 may include at least one neural network. The neural network may include network models such as a Deep Neural Network (DNN), a Recurrent Neural Network (RNN), a Bidirectional Recurrent Deep Neural Network (BRDNN), a Multilayer Perceptron (MLP) network, and a Convolutional Neural Network (CNN), but is not limited thereto.

For example, the second artificial neural network model 400 may be a model constructed by learning the correlation between at least one sub-sampled magnetic resonance image and at least one fully sampled magnetic resonance image by using a neural network on the basis of every pixels of at least one sampling line stacked along a phase encoding direction Ky.

Furthermore, the second artificial neural network model 400 may be constructed using various types of additional data other than the sub-sampled magnetic resonance image and the fully sampled magnetic resonance image. For example, at least any one of k-space data, real image data, imaginary image data, size image data, and phase image data corresponding to the first magnetic resonance image 240 may be used as the additional data.

A method in which the second artificial neural network model 400 performs learning and reconstruction additionally using scan parameters will be described below.

Figure 7:
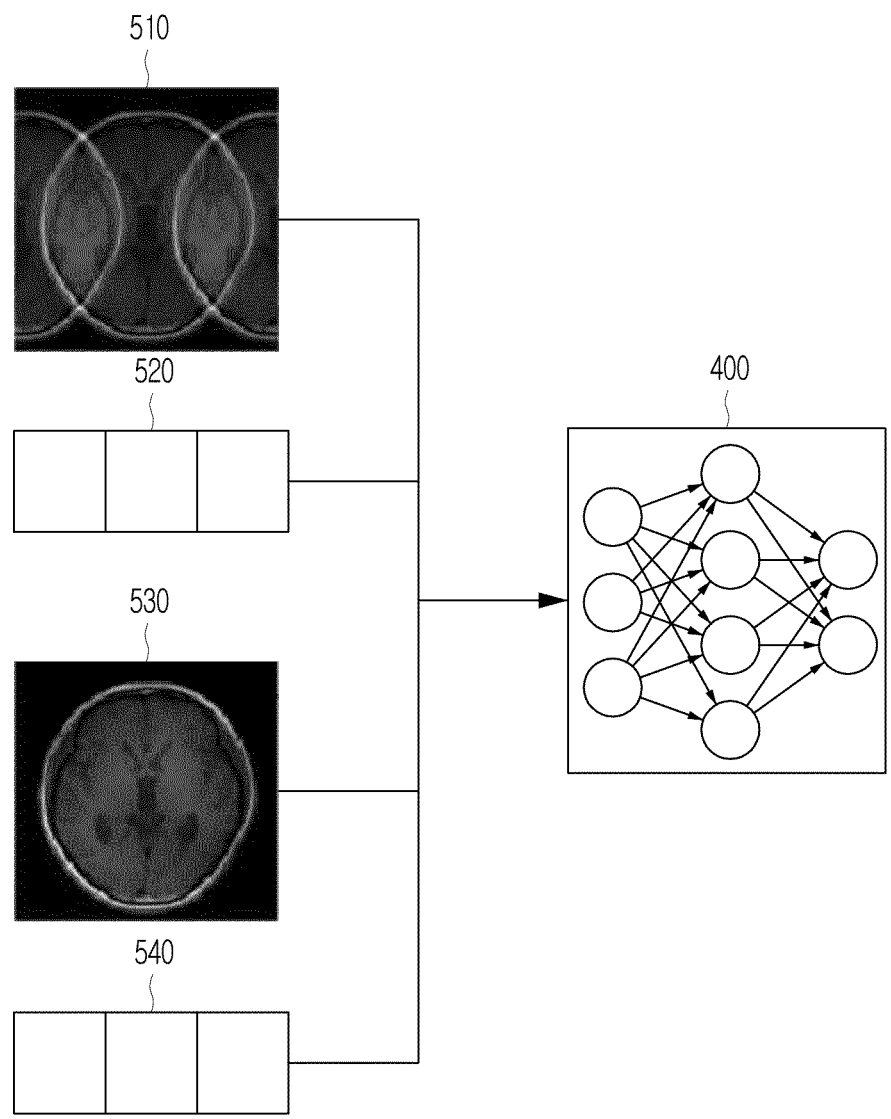
FIG. 7 is a schematic diagram showing a method of training a second artificial neural network model according to an embodiment of the present invention.

FIG. 7 is a schematic diagram showing a method of training a second artificial neural network model according to an embodiment of the present invention.

In the present specification, a low-quality magnetic resonance image is referred to as a training image 510, and a high-quality magnetic resonance image is referred to as a label image 530. For example, the training image 510 may mean an image acquired by sub-sampling a magnetic resonance signal, and the label image 530 may mean an image acquired by fully sampling a magnetic resonance signal. For example, the number of excitations of the training image 510 may be smaller than that of the label image 530. For example, the phase resolution of the training image 510 may be lower than that of the label image 530. The differences between the training image 510 and the label image 530 may be various, but are not limited thereto.

Meanwhile, imaging may be performed once in order to acquire the training image 510 and the label image 530, and the training image 510 and the label image 530 may be generated by performing pre-processing using a magnetic resonance signal acquired through the imaging performed once.

Referring to FIG. 7, the second artificial neural network model 400 may receive not only the training image 510 and the label image 530, but also a first parameter group 520 including at least one scan parameter used for the magnetic resonance imaging of the training image 510 and a second parameter group 540 including at least one scan parameter used for the magnetic resonance imaging of the label image 530. Accordingly, the second artificial neural network model 400 may learn the correlation between the low-quality training image 510 and the high-quality label image 530.

Scan parameters refer to environmental variables set in the process of acquiring a magnetic resonance image. Depending on the values of scan parameters, an acquired magnetic resonance signal may vary, and a reconstructed magnetic resonance image may also vary. More specifically, the imaging time, resolution, noise and the like of a magnetic resonance image may be adjusted by setting scan parameters.

For example, scan parameters may include the number of excitations (NEX), a phase resolution, and an acceleration factor, which are merely examples, but are not limited thereto.

More specifically, the number of excitations means the number of repetitions at the time when lines of a magnetic resonance signal are repeatedly acquired in a k-space. The number of excitations may be referred to as the number of averages. As the number of excitations increases, the imaging time of a magnetic resonance image may increase proportionally. For example, in the case where the number of excitations is 2 or more, when the number of excitations is set to a reduced number and then a magnetic resonance image is imaged, the imaging time may be shortened.

A phase resolution refers to a value obtained by dividing the number of lines, sampled in a phase encoding direction in a k-space, by a preset reference value. For example, the phase resolution may have values of 0.5, 0.8, 1.0, etc. As the phase resolution increases, the imaging time of a magnetic resonance image may increase proportionally. Accordingly, when the phase resolution is set to a reduced value and then a magnetic resonance image is imaged, the imaging time may be shortened.

The acceleration factor is a term used in a parallel imaging technique, and refers to a value obtained by dividing the number of signal lines sampled fully in a k-space by the number of signal lines sub-sampled through accelerated imaging. For example, the fact that the acceleration factor is 2 may mean that when lines are acquired by sampling a magnetic resonance signal in a phase encoding direction, a number of signal lines equal to the half of the number of fully sampled signal lines are acquired, for example, that lines are acquired at two-line intervals. As the acceleration factor increases, the imaging time of a magnetic resonance image may decrease proportionally.

In FIG. 7, the size of each of the first parameter group 520 and the second parameter group 540 may be 3 because it includes values for the number of excitations, a phase resolution, and an acceleration factor when it acquires the training image 510 or the label image 530. This is only an example, and the size of each of the first parameter group 520 and the second parameter group 540 may vary depending on the types of scan parameters that are included in the corresponding parameter group 520 or 540.

According to an embodiment of the present disclosure, tasks to be performed in the process of reconstructing a magnetic resonance image may be determined according to scan parameter values applied to magnetic resonance imaging. For example, at least one of a pre-processing algorithm and a post-processing algorithm applied to the training image 510 may be determined according to a scan parameter value included in the first parameter group 520. Furthermore, at least one of a pre-processing algorithm and a post-processing algorithm applied to the label image 530 may be determined according to a scan parameter value included in the second parameter group 540. For example, tasks such as denoising, super resolution and the like may be performed in a reconstruction process according to the number of excitations, a phase resolution, and an acceleration factor.

Accordingly, when a reconstructed image is generated by taking into consideration scan parameters in a magnetic resonance image processing process, the accuracy of image reconstruction may be improved. Furthermore, a setting may be made such that a reconstructed image of the degree desired by a user can be output by adjusting the second parameter group 540 input in the step of training the second artificial neural network model 400.

Figure 8:
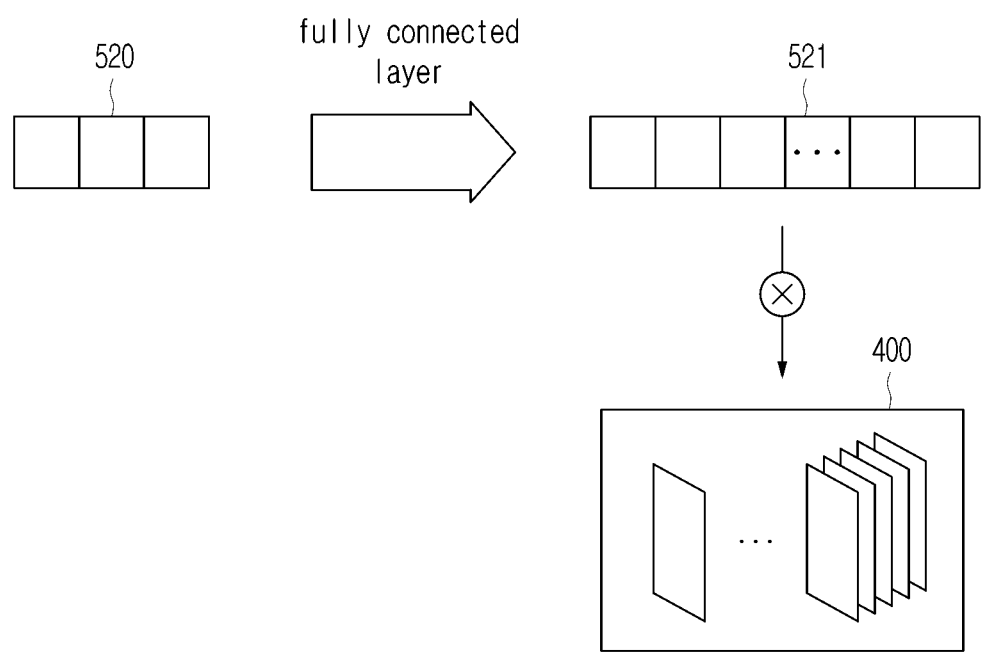
FIG. 8 is a schematic diagram showing a method of inputting scan parameters to a second artificial neural network model according to an embodiment of the present invention.

FIG. 8 is a schematic diagram showing a method of inputting scan parameters to a second artificial neural network model according to an embodiment of the present invention.

Referring to FIG. 8, the first parameter group 520 is one-dimensional data that lists scan parameter values, and a training image corresponding to the first parameter group 520 is two-dimensional data. Accordingly, pieces of data having different dimensions may not be concatenated and input to one artificial neural network model, so that it is necessary to transform the first parameter group 520.

As an embodiment, first attention data 521 may be generated by inputting the first parameter group 520 to a pre-processing artificial neural network model. The first attention data 521 may represent the weights at which scan parameters included in the first parameter group 520 are multiplied by specific layer channels of the second artificial neural network model 400. For example, the pre-processing artificial neural network model may be configured as a fully connected layer.

Some layers of the second artificial neural network model 400 are multiplied by the first attention data 521 along the axes of channels. For example, the some layers may include a layer located at the back of the second artificial neural network model 400.

Although the pre-processing artificial neural network model is not limited to a specific one, it may be designed such that the length of the first attention data 521 and the number of channels of the layers to be multiplied by the first attention data 521 correspond to each other.

Although the pre-processing artificial neural network model is shown as being separate from the second artificial neural network model 400 in FIG. 8, this is only an example, and the pre-processing artificial neural network model and the second artificial neural network model 400 may be implemented as a single artificial intelligence model. Alternatively, each of the pre-processing artificial neural network model and the second artificial neural network model 400 may be implemented as a plurality of artificial intelligence models.

Meanwhile, although FIG. 8 illustrates the first parameter group 520 as an example, the above description may be applied to the second parameter group 540 in a similar manner. In other words, the second parameter group 540 may be input to the pre-processing artificial neural network model to generate second attention data, and the second attention data may be input to the second artificial neural network model 400. Alternatively, the first parameter group 520 and the second parameter group 540 may be input to the pre-processing artificial neural network model together, and attention data may be output.

Figure 9:
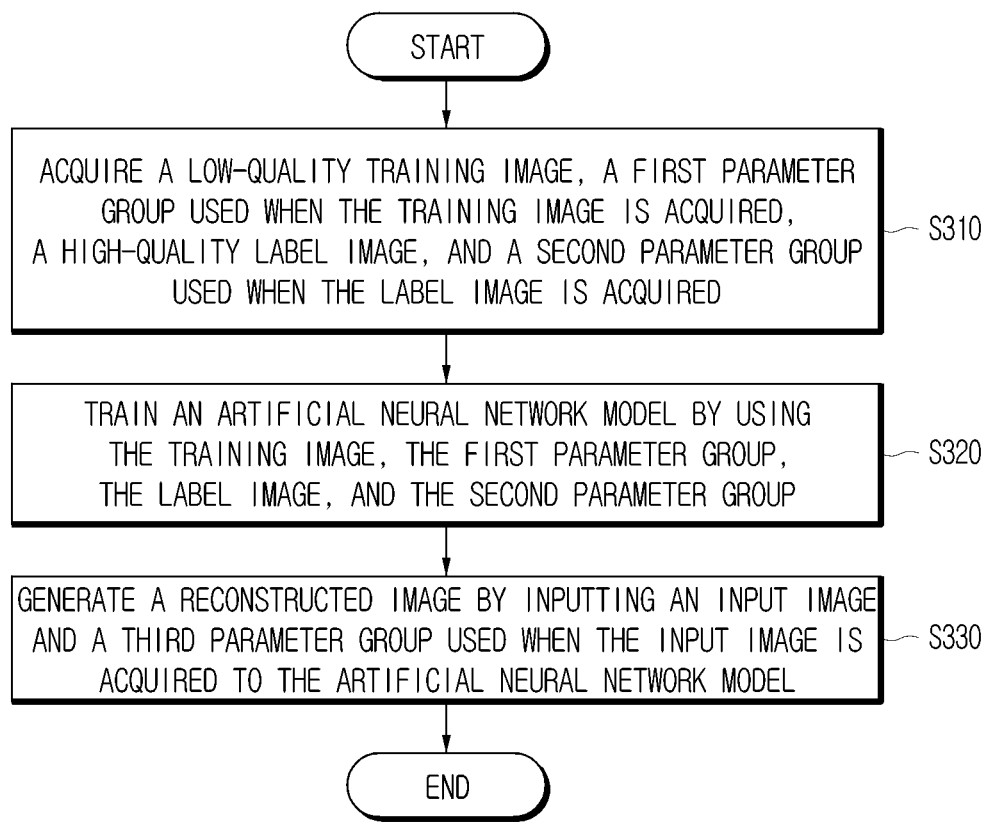
FIG. 9 is a flowchart showing the sequence of a magnetic resonance image processing method using scan parameters according to an embodiment of the present invention.

FIG. 9 is a flowchart showing the sequence of a magnetic resonance image processing method using scan parameters according to an embodiment of the present invention.

Referring to FIG. 9, a magnetic resonance image processing apparatus may acquire a low-quality training image, a first parameter group including scan parameters used to acquire the training image, a high-quality label image, and a second parameter group including scan parameters used to acquire the label image in step S310. As described above, the training image may have a smaller number of samplings, a smaller number of excitations, or a lower phase resolution than the label image.

The magnetic resonance image processing apparatus may train an artificial neural network model by using the training image, the first parameter group, the label image, and the second parameter group in step S320. More specifically, the artificial neural network model may receive the training image, the first parameter group, and the second parameter group as input data, and may also receive the label image as label data. For example, the artificial neural network model may correspond to the artificial neural network model 400 of FIGS. 3, 6, 7, and 8.

In this case, the magnetic resonance image processing apparatus may perform pre-processing so that the size of the first parameter group and the size of the second parameter group correspond to the number of channels of the artificial neural network model.

More specifically, the magnetic resonance image processing apparatus may generate first attention data and second attention data by inputting the first parameter group and the second parameter group to the pre-processing artificial neural network model, and may input the first attention data and the second attention data to the artificial neural network model. In this case, the pre-processing artificial neural network may refer to the fully connected layer of FIG. 8.

The magnetic resonance image processing apparatus may generate a reconstructed image by inputting an input image and a third parameter group including scan parameters used to acquire the input image to the trained artificial neural network model in step S330.

The description of the present invention described above is illustrative, and those of ordinary skill in the art to which the present invention pertains can appreciate that the present invention may be easily modified into other specific forms without changing the technical spirit or essential features of the present invention. Therefore, it should be understood that the embodiments described above are illustrative and not restrictive in all respects. For example, each component described as being in a single form may be implemented in a distributed form. In the same manner, components described as being in a distributed form may be implemented in a combined form.

The scope of the present invention is defined by the following claims rather than the above detailed description, and all changes or modifications derived from the meanings and scope of the claims and their equivalent concepts should be interpreted as being encompassed within the scope of the present invention.

DESCRIPTION OF REFERENCE SYMBOLS

100: magnetic resonance image processing apparatus
110: communication module
120: memory
130: processor
140: database
210: sub-sampled magnetic resonance signal
220: first k-space data
230: second k-space data
240: first magnetic resonance image
250: second magnetic resonance image

What is claimed is:

1. A magnetic resonance image processing method performed by a magnetic resonance image processing apparatus, the method comprising:
acquiring a low-quality training image, a first parameter group including at least one scan parameter applied, which is an environmental variable applied to a medical imaging device that captures the training image, when the training image is acquired, a high-quality label image, and a second parameter group including at least one scan parameter applied, which is an environmental variable applied to the medical imaging device that captures the label image, when the label image is acquired; and
training an artificial neural network model by using the training image, the first parameter group, the label image, and the second parameter group,
wherein the first parameter group and the second parameter group are one-dimensional data in which values of at least one scan parameter are listed, and
wherein the first parameter group and the second parameter group are transformed and input to the artificial neural network model.

2. The magnetic resonance image processing method of claim 1, wherein the scan parameter includes at least one of:
a number of excitations, which is a number of repetitions when lines of first k-space data of a magnetic resonance signal are repeatedly acquired; a phase resolution, which is a value obtained by dividing a number of lines sampled in a phase encoding direction of the first k-space data by a preset reference value; and an acceleration factor, which refers to a value obtained by dividing a number of fully sampled signal lines of the first k-space data by a number of sub-sampled signal lines.

3. The magnetic resonance image processing method of claim 1, wherein:
the training image is acquired by sub-sampling a magnetic resonance signal; and
the label image is acquired by fully sampling the magnetic resonance signal.

4. The magnetic resonance image processing method of claim 1, wherein a number of excitations of the training image is smaller than a number of excitations of the label image.

5. The magnetic resonance image processing method of claim 1, wherein a phase resolution of the training image is lower than a phase resolution of the label image.

6. The magnetic resonance image processing method of claim 1, wherein training the artificial neural network model comprises performing pre-processing so that a size of the first parameter group and a size of the second parameter group correspond to a number of channels of the artificial neural network model.

7. The magnetic resonance image processing method of claim 6, wherein:
performing the pre-processing comprises generating first attention data and second attention data by inputting the first parameter group and the second parameter group to a pre-processing artificial neural network model; and
training the artificial neural network model comprises inputting the first attention data and the second attention data to the artificial neural network model.

8. The magnetic resonance image processing method of claim 7, wherein the pre-processing artificial neural network model includes a fully connected layer.

9. The magnetic resonance image processing method of claim 1, further comprising generating a reconstructed image by inputting an input image and a third parameter group, including at least one scan parameter applied when the input image is acquired, to the artificial neural network model.

10. A non-transitory computer-readable storage medium in which a program for performing the method of claim 1 is stored.

11. A magnetic resonance image processing method performed by a magnetic resonance image processing apparatus, the method comprising:
inputting an input image and a third parameter group, including at least one scan parameter applied, which is an environmental variable applied to a medical imaging device that captures the input image, when the input image is acquired, to an artificial neural network model trained using a low-quality training image, a first parameter group including at least one scan parameter applied, which is an environmental variable applied to a medical imaging device that captures the training image, when the training image is acquired, a high-quality label image, and a second parameter group including at least one scan parameter applied, which is an environmental variable applied to the medical imaging device that captures the label image, when the label image is acquired; and
outputting a reconstructed image from the artificial neural network model,
wherein the first parameter group, the second parameter group and the third parameter group are one-dimensional data in which values of at least one scan parameter are listed,
wherein the first parameter group and the second parameter group are transformed and input to the artificial neural network model.

12. A magnetic resonance image processing apparatus for performing a magnetic resonance image processing method, the magnetic resonance image processing apparatus comprising:
memory configured to store a magnetic resonance image processing program; and
a processor configured to execute the program,
wherein the processor trains an artificial neural network model by using a low-quality training image, a first parameter group including at least one scan parameter applied, which is an environmental variable applied to a medical imaging device that captures the training image, when the training image is acquired, a high-quality label image, and a second parameter group including at least one scan parameter applied, which is an environmental variable applied to the medical imaging device that captures the label image, when the label image is acquired, wherein the first parameter group and the second parameter group are one dimensional data in which values of at least one scan parameter are listed, wherein the first parameter group and the second parameter group are transformed and input to the artificial neural network model.

\* \* \* \* \*